United States Patent [19]

Brana et al.

[11] Patent Number: 5,183,821

[45] Date of Patent: Feb. 2, 1993

[54] METHOD FOR TREATING LEUKEMIAS USING N-(2-DIMETHYLAMINOETHYL)-3-AMINO-1,8-NAPHTHALIMIDE FOR TREATING LEUKEMIAS AND SOLID TUMORS

[75] Inventors: Miguel F. Brana; Antonio M. Sanz; Rafael P. Alvarez-Ossorio; Cristobal M. Roldan; Cristina R. F. De Gamboa; Jesus G. Garcia; Jose M. C. Berlanga, all of Madrid, Spain

[73] Assignee: Laboratories Knoll, S.A., Madrid, Spain

[21] Appl. No.: 728,025

[22] Filed: Jul. 8, 1991

Related U.S. Application Data

[63] Continuation of Ser. No. 296,340, Jan. 9, 1989, abandoned, which is a continuation of Ser. No. 864,009, May 16, 1986, abandoned, which is a continuation-in-part of Ser. No. 533,542, Sep. 19, 1983, abandoned.

[51] Int. Cl.$^5$ ............................................. A61K 31/445
[52] U.S. Cl. .................................... 514/296; 546/100
[58] Field of Search .................... 546/100; 514/296

[56] References Cited

U.S. PATENT DOCUMENTS

| 1,796,012 | 3/1931 | Eckert | 546/100 |
| 2,088,978 | 5/1963 | Brunner et al. | 564/423 |
| 3,192,263 | 6/1965 | Spiegler | 564/423 X |
| 3,230,259 | 1/1966 | Levy | 564/423 |
| 4,204,063 | 5/1980 | Brana et al. | 546/99 |
| 4,499,266 | 2/1985 | Cheng et al. | 544/126 |
| 4,594,346 | 6/1986 | Zee-Cheng et al. | 514/296 X |
| 4,665,071 | 5/1987 | Zee-Cheng et al. | 514/296 X |
| 4,714,689 | 12/1987 | Stammann et al. | 564/423 X |

OTHER PUBLICATIONS

Fieser et al., "Reagents for Organic Synthesis", vol. 1, (1967), p. 440; John Wiley & Sons, N.Y.
*Drug Res.*, vol. 34, pp. 1243-1246 (1984), Paull et al.
*European J. of Med. Chem.*, vol. 16, pp. 207-212 (1981), Brana et al.
*Revista Espanola de Oncologia*, vol. 29, pp. 439-444 (1982), Stockert et al.

*Primary Examiner*—Joseph Paul Brust
*Attorney, Agent, or Firm*—Oblon, Spivak, McClelland, Maier & Neustadt

[57] ABSTRACT

N-(2-dimethylaminoethyl)-3-amino-1,8-naphthalimide (amonafide) is an effective agent for the treatment of leukemias and solid tumors.

6 Claims, No Drawings

METHOD FOR TREATING LEUKEMIAS USING N-(2-DIMETHYLAMINOETHYL)-3-AMINO-1,8-NAPHTHALIMIDE FOR TREATING LEUKEMIAS AND SOLID TUMORS

This application is a continuation of U.S. patent application Ser. No. 07/296,340, filed Jan. 9, 1989, now abandoned, which was a continuation of application Ser. No. 06/864,009, filed May 16, 1986, now abandoned, which was a continuation-in-part of application Ser. No. 06/533,542, filed Sep. 19, 1983, now abandoned.

BACKGROUND OF THE INVENTION

1. Field of the Invention

This invention relates to a method for treating leukemias and solid tumors in human patients.

2. Discussion of the Background

U.S. Pat. No. 4,204,063 discloses a series of substituted naphthalimides and derivatives thereof, such as the salts thereof with pharmacologically acceptable acids, N-oxides, etc. In the "BACKGROUND OF THE INVENTION" cytotoxic activity of 33 compounds is shown by means of its $ID_{50}$ of HeLa cells cultured in a monolayer on glass bottles. Cytotoxic activity "in vitro" is the single activity data shown in the Brana et al patent.

It will be shown, in the next paragraphs, that antileukemic activity "in vivo" is not obvious from cytotoxic activity "in vitro", neither qualitatively nor quantitatively.

Experiments in HeLa cells predict cyctostatic and/or cytotoxic activity, which is considered to be a pre-screening step in the selection of anti-tumoral drugs. However, simply determining the $ID_{50}$ in HeLa cells is not necessarily a predictor of anti-leukemia activity.

"In vitro" data is a poor predictor of antileukamic activity, because the results obtained from the technology of cultivating human cells are just or generic value (Llombart-Rodriguez, "Pruebas experimentales de control". In "Compendio de la doctrina cancerologica y de su problematic actual". Ed. "Caja de Ahorros Provincial de Guipuzcoa" (1983) pp. 411–421), inasmuch as they obviate the phenomena of toxicity, absorption, distribution, metabolism, elimination and response of the host that can modify the results obtained "in vitro" (Connors, 1969).

Tests "in vitro" can give rise to the appearance of "false positive" (assignment of antitumor activity to a drug not having such activity in the "in vivo" test) and to "false negatives" (rejection of an active drugs "in vivo" through not having shown activity "in vitro").

In summary, cell culture tests are inappropriate for determinations of anti-leukemia effect.

On the other hand, murine transplantable leukemias are a good predictor of anti-leukemia activity in human beings (Kenis "Dose schedules and mode of administration of chemotherapeutic agents in man". Recent Results Cancer Res. 21, 54–61 (1969). Only those tests which use the survival times as an activity parameter are valid as predictors of antileukemia activity in human beings (for instance, leukemia p388 y L-1210), whilst "in vitro" tests (HeLa cells and other) are inappropriate (Llombart-Rodriguez, 1983). NCI data generated in the last years confirm the value of above assertions to compounds of general formula

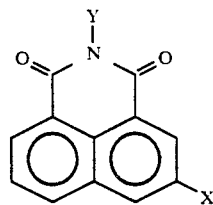

as described in U.S. Pat. No. 4,204,063.

From these data, shown below, cytotoxic activity in HeLa cells does not make obvious antileukemic activity against leukemia P388, a good predictor of antitumoral activity in human beings (Kenis, 1969; Llombart Rodriguez, 1983; World Health Organization, "Quimioterapia de los Tumores Solidos, Technical Report No. 605, Geneva, 1977") thereafter the Brana et al patent can not be considered as prior art in the field of utilization of present application.

U.S. Pat. No. 4,204,063 shows the cytotoxic activity of 33 compounds. 14 of them have been studied for NCI against leukemia P388. These are the compounds of examples 3, 4, 9, 10, 11, 12, 13, 24, 26, 27, 28, 29, 30 and 31. The compound of Example 9 is the compound of the present application.

The significance of X and Y in each case are indicated in the next table:

| EXAMPLE | X | Y |
|---|---|---|
| 3 | $NO_2$ | $CH_2-CH_2-CH_2-N(CH_2-CH_3)_2$ |
| 4 | $NO_2$ | $CH_2-CH_2-N\underset{\diagdown\_\_\diagup}{\diagup^{\frown}\diagdown}O$ |
| 9 | $NH_2$ | $CH_2-CH_2-N(CH_3)_2$ |
| 10 | $NH_2$ | $CH_2-CH_2-N(CH_2-CH_3)_2$ |
| 11 | $NH_2$ | $CH_2-CH_2-N\underset{\diagdown\_\diagup}{\diagup^{\frown}\diagdown}$ |
| 12 | $NH_2$ | $CH_2-CH_2-N\underset{\diagdown\_\_\diagup}{\diagup^{\frown}\diagdown}$ |
| 13 | $NH_2$ | $CH_2-CH_2-N\underset{\diagdown\_\_\diagup}{\diagup^{\frown}\diagdown}O$ |
| 24 | OH | $CH_2-CH_2-N\underset{\diagdown\_\_\diagup}{\diagup^{\frown}\diagdown}O$ |
| 26 | $OCH_3$ | $CH_2-CH_2-N(CH_3)_2$ |
| 27 | $OCH_3$ | $CH_2-CH_2-N\underset{\diagdown\_\diagup}{\diagup^{\frown}\diagdown}$ |
| 28 | $NHCO_2C_2H_5$ | $CH_2-CH_2-N(CH_3)_2$ |

-continued

| EXAMPLE | X | Y |
|---|---|---|
| 29 | NHCO$_2$C$_2$H$_5$ | CH$_2$—CH$_2$—N⟨pyrrolidine⟩ |
| 30 | NHCOCH$_3$ | CH$_2$—CH$_2$—N(CH$_3$)$_2$ |
| 31 | NHCOCH$_3$ | CH$_2$—CH$_2$—N⟨pyrrolidine⟩ |

Experimental results from NCI studies against leukemia P388 are shown in an appendix (Appendix 1). In order to simplify the presentation of results we have extracted from these the minor active dose (MDA) against leukemia P388—for each compound. MDA is defined as the minor dose of the drug that reaches the minimal activity criteria of the NCI. For leukemia P388 this criteria on the basis of survival time is a minimal increase in survival of treated animals over a control resulting in a T/C≧120. In the following table the MDA for 14 examples are presented. In cases where none of the tested doses reached the MDA, the MDA is indicated as "NONE". The column "cytotoxic activity" has been extracted from U.S. Pat. No. 4,204,063. Data are presented in order of the highest to lowest cytotoxic activity.

TABLE I

| Example | Cytotoxic Activity "in vitro" ID$_{50}$ in HeLa cells (mcg/ml) | Antileukemic Activity "in vitro" MDA against leukemia P388 (mg/kg) |
|---|---|---|
| 27 | 0.75 | NONE |
| 11 | 1.5 | 6.5 |
| 26 | 1.5 | 18.9 |
| 9 | 2.5 | 2.0 |
| 10 | 3.0 | 3.2 |
| 24 | 3.5 | 240 |
| 30 | 4.0 | 3.75 |
| 31 | 5.0 | 30 |
| 4 | 6.0 | NONE |
| 12 | 8.0 | NONE |
| 28 | 10.0 | 30 |
| 29 | 10.0 | 30 |
| 13 | 10.0 | NONE |
| 3 | 20.0 | NONE |

This table shows clearly that antileukemic activity is not obvious from cytotoxic activity, because 5 of 14 compounds studied, all of them with greater or lesser cytotoxic activity, did not show antileukemic activity at all. Moreover in the 9 compounds with both cytotoxic and antileukemic activity, is not possible to establish a correlation between active doses "in vitro" and "in vivo". Because of this, data shown in the column marked ANTILEUKEMIC ACTIVITY can not be deduced from the column CYTOTOXIC ACTIVITY. The correlation index r=0.00106 (n=9) obtained from data of 9 cases with both activities is statistically non significant.

Thus, in conclusion, for compounds of the general formula

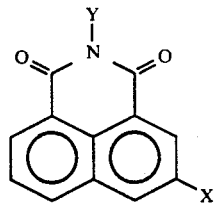

it is not possible to predict antileukemic activity against leukemia P388 from cytotoxic activity in HeLa cells, neither qualitatively nor quantitatively.

As leukemia P388 is a better predictor of antitumoral activity in human beings than cytotoxic activity, it is deduced that the Brana et al patent can not be considered prior art in the field of utilization of the instant invention.

SUMMARY OF THE INVENTION

Accordingly, it is an object of the present invention to provide a method for treating leukemias and solid tumors.

This object has been achieved by the inventors' discovery that amonafide is an effective agent for treating leukemias and solid tumors.

DETAILED DESCRIPTION

The activity of the compound disclosed in Example 9 of U.S. Pat. No. 4,204,063 (hereinafter, "the compound" or "NSC 308847") has been demonstrated by experiments carried out under the auspices of the National Cancer Instituted, Division of Cancer Treatment. On the basis of the results obtained in a series of antitumor screens, which demonstrated the utility of the compound in treating leukemias and solid tumors, the Decision Network Comittee of the Division of Cancer Treatment, Natuional Cancer Institute (NCI) selected the compound for clinical trials.

ANTITUMOR ACTIVITY

A summary of experimental data obtained by NCI is shown in the next table.

TABLE II

| HOST GROUP | TUMOR | PARAMETER | INOCULUM SITE | TESTS PROCESSED | EVALUATION |
|---|---|---|---|---|---|
| Mouse | B16 Melanocarcinoma | Median survival time | Intraperitoneal | 28 | Reproducible minimal activity |
| Mouse | DC8F$_1$ Mammary tumor | Change in median tumor weight | Subcutaneous | 15 | Activity not confirmed |
| Mouse | CX-1 Colon menograft | Change in average tumor diameter | Intrarenal or Subrenal capsule | 4 | Activity not confirmed |
| Mouse | Colon 38 | Median tumor weight estimated from tumor diameter | Subcutaneous | 25 | Reproducible minimal activity |
| Mouse | L-1210 Lymphoid Leukemia | Mean survival time | Intraperitoneal | 12 | Activity substantially greater than the minimal |
| Mouse | L-1210 Lymphoid Leukemia | Median survival time | Intraperitoneal | 21 | Activity substantially greater than the minimal |

TABLE II-continued

| HOST GROUP | TUMOR | PARAMETER | INOCULUM SITE | TESTS PROCESSED | EVALUATION |
|---|---|---|---|---|---|
| Mouse | L-1210 Lymphoid Leukemia | Median survival time | Subcutaneous | 16 | Activity substantially greater than the minimal |
| Mouse | LX-1 lung menograft | Change in average tumor diameter | Intrarenal or subrenal capsule | 4 | Activity not confirmed |
| Mouse | Lewis lung carcinoma | Median survival time | Intravenous | 12 | Activity not confirmed |
| Mouse | MX-1 Breast menograft | Change in average tumor diameter | Intrarenal or subrenal capsule | 4 | Activity not confirmed |
| Mouse | P388 Lymphocytic leukemia | Median survival time | Intraperitoneal | 9 | Reproducible minimal activity |
| Mouse | M5076 ovarian carcinoma | Mean survival time | Intraperitoneal | 15 | Activity Substantially greater than the minimal |

As shown in Table II the compound has been evaluated as having activity substantially greater than the level considered to be of minimal interest for full clinical evaluation in the treatment of lymphoid leukemia and M5076 ovarian carcinoma. In addition, the results confirm at least a reproducible minimal activity of the compound against B16 melanocarcinoma, colon 38 tumors and P388 lymphocytic leukemia.

The activity of the compound has been evaluated by experiments carried out under the auspices of the Division of Cancer Treatment, National Cancer Institute, employing techniques considered to be reliable indicators of chemotherapeutic utility in the treatment of forms of cancer in human patients. The details of the methodology employed in the reported experiments may be determined with reference to established NCI screening methods.

In the experiments conducted by the NCI, evaluation of activity is made on the basis of appropriate parameters, such as median survival time (MST) or change in average tumor diameter (CATD)in ocular micrometer units (OMU). On the basis of these evaluations, the Division of Cancer Treatment of the NCI selects a very small number of compounds each year from a large number of potential candidates for further evaluation, primarily because of the correlation which has been found between the results of the screening methods and demonstrations of therapeutic activity in human patients.

The compound was found initially to be active in the P388 leukemia pre-screen, with T/C values (ratio of Test (T) evaluation to control (C) evaluation expressed as a percentage) of 177 and 176. Both values exceed the minimum T/C values for interest by the Decision Network Committe.

The compound was then schedule for testing in the tumor panel, which consisted of the B16 melanoma, Colon 38, L1210 leukemia, CD8F1 Mammary, Lewis lung Carcinoma and three human xenograft tumors (Colon, Lung, Mammary). Its T/C value also exceeded the minimal level of activity for clinical interest in the L1210 leukemia screen and the material was active in both the B16 and Colong 38 tumor models, although not at a sufficient level of activity to be of immediate clinical interest. Further, the compound was scheduled for testing in M5076 ovarian carcinoma. Its T/C value also exceeded the minimal level of activity for clinical interest in this non-leukemic tumor.

In additional tests, the compound was shown to meet the National Cancer Institute, Division of Cancer Treatment Decision Network Committe activity criterial in the i.p. implanted murine L1210 lymphoid leukemia system. In three experiments, optimal increased life spans (ILS) of 75–117% (mean=96%) were obtained following i.p. administration of 16 mg/kg on days 1–9. In one other experiment, the compound was not active as tested. Activity (ILS≧25%) was observed over a two-fold dosage range.

The compound also demonstrated activity against three other murine tumor systems, In the i.p. implanted P388 lymphocytic leukemia system, maximum increased life spans of 76 and 77% were obtained following i.p. administration of 8 and 16 mg/kg, respectively, on days 2–9. Against the i.p. implanted B16 melanoma, activity (ILS≧25%) was observed in three experiments; increased life spans of 37–55% were obtained following i.p. administration of 16 mg/kg on days 1–9. The growth of the s.c. implanted colon 38 tumor was also inhibited by 83% (T/C=17%) following i.p. administration of 64 mg/kg.

The compound was not observed to be effective against the murine CD8F$_1$ mammary tumor and Lewis lung carcinoma, and was not active against the human CX-1 colon, LX-1 lung and MX-1 mammary tumor xenografts implanted beneath the renal capsule of athymic mice.

While the compound was generally tested as a suspension in Tween-80, in one L1210 experiment it was tested as a solution in 0.1 N HCL diluted with saline. The level of activity (ILS=117%) was maintained. The solubilities of the compound in 0.01 N and 0.1 HCl are approximately 3 and 30 mg/ml, respectively.

As disclosed in U.S. Pat. No. 4,204,063, the compound may be prepared by reaction of 3-amino-1,8-naphthalic anhydride and 2-dimethylaminoethylamine in a suitable solvent at temperatures in the range of from the freezing point to the boiling point of the solvent, ambient temperature being effective in the majority of cases. Once the reaction is completed, the resulting product is filtered and recrystallized in an appropriate solvent. In the process disclosed in the patent, the reaction is carried out in ethanol and the product recrystallized from chloroform-n-hexane. The product consists of yellow needles with a melting point of 171°–173° C. (ethanol).

Another improved method for obtaining the compound comprises subjecting 2-(2-dimethylaminoethyl)-5-nitrobenzo (d,e) isoquinolin-1,3-dione [N-(2-dimethylaminoethyl)-3-nitro-1,8-napthalimide] to a reduction with hydrazine as reducing agent using a palladium on carbon catalyst. The compound is obtained in quantitative yield.

In an illustrative example, 3.0 kg of 2-(2-dimethylaminoethyl)-5-nitrobenzo (d,e) isoquinolin-1,3-dione and 75 g of 10% Pd on carbon in 75 l ethanol was refluxed until the nitro compound was dissolved. 3.0 l of 80% hydrazine hydrate was added slowly over 0.5 h with stirring, the mixture refluxed with stirring for 3.5 h and then filtered. The mixture was cooled overnight to room temperature. Filtration gave 2.6 kg of impure product, which was recrystallized from ethanol to give 2.100 kg of the pure compound, m.p. 171°–173° C.

The compound may be administered in a manner known per se, in particular, by intraperitoneal injection or other parenteral routes in a suitable carrier, such as saline solution. The appropriate dosage for treatment of a given form of leukemia or solid tumor may be readily determined with reference to the patients' degree of illness, body weight, general physical condition and so on. In general, the compound may be administered in doses of from about 1 mg/kg to about 64 mg/kg of patient body weight; in particular, dosages in the range of 2–32 mg/kg, and especially about 16 mg/kg of body weight are effective.

The following summaries of experiments further demonstrate the compound's utility in the treatment of leukemias and other forms of cancer.

EXPERIMENT 1

Method

Host: Mouse $CD_2F_1$ ($CDF_1$)
Tumor: L-1210 Lymphoid leukemia
Inoculum Site: intraperitoneal
Tissue: Ascitic Fluid
Level: $10^4$ cells
Route: Intraperitoneal
Vehicle: Acid Diluted with saline
Total injections: 9
Treatment schedule (relative to tumor inoculation day): daily on days 1–9
Day of evaluation (relative to tumor inoculation day): 30
Parameter: Median survival time (MST) in days
NCI minimal activity criteria: Percent T/C ≧ 125
Percent T/C: Ratio of test (T) evaluation to control (C) evaluation expressed as a percentage

| | | | Results | | | |
|---|---|---|---|---|---|---|
| Animal number | Sex | Sample | Route | Doses mg/kg | Parameter Evaluation | Percent T/C |
| 33 | | Control | | | 9.2 | |
| 6 | Male | NSC 308847 | i.p. | 32.00 | 8.8 | 95 |
| 6 | Male | NSC 308847 | i.p. | 16.00 | 20.0 | 217 |
| 6 | Male | NSC 308847 | i.p. | 8.00 | 12.3 | 133 |
| 6 | Male | NSC 308847 | i.p. | 4.00 | 10.4 | 113 |
| 6 | Male | NSC 308847 | i.p. | 2.00 | 9.9 | 107 |

EXPERIMENT 2

Method

Host: Mouse $CD_2F_1$ ($CDF_1$)
Tumor: L-1210 Lymphoid leukemia
Inoculum site: Subcutaneous
Tissue: Ascitic fluid
Level: $10^5$ cells
Route: Intraperitoneal
Vehicle: Acid diluted with saline
Total injections: 9
Treatment schedule (relative to tumor inoculation day): daily on days 1–9
Day of evaluation (relative to tumor inoculation day): 30
Parameter: Median survival time (MST) in days
NCI minimal activity criteria: Percent T/C ≧ 125
Percent T/C: Ratio of test (T) evaluation to control (C) evaluation expressed as a percentage

| | | | Results | | | |
|---|---|---|---|---|---|---|
| Animal number | Sex | Sample | Route | Doses mg/kg | Parameter Evaluation MST | Percent T/C |
| 30 | | Control | | | 8.0 | |
| 6 | Female | NSC 308847 | i.p. | 24.00 | 9.3 | 116 |
| 6 | Female | NSC 308847 | i.p. | 16.00 | 12.0 | 150 |
| 6 | Female | NSC 308847 | i.p. | 10.00 | 9.0 | 112 |
| 6 | Female | NSC 308847 | i.p. | 7.00 | 8.3 | 103 |
| 6 | Female | NSC 308847 | i.p. | 5.00 | 8.2 | 102 |

EXPERIMENT 3

Method

Host: Mouse $CD_2F_1$ ($CDF_1$)
Tumor: L-1210 Lymphoid leukemia
Inoculum Site: intraperitoneal
Tissue: Ascitic fluid
Level: $10^5$ cells
Route: Intraperitoneal
Vehicle: Saline with Tween-80
Total injections: 9
Treatment schedule (relative to tumor inoculation day) daily on days 1–9
Day of evaluation (relative to tumor inoculation day): 30
Parameter: Mean survival time (MST) in days.
NCI minimal activity criteria: Percent T/C ≧ 125
Percent T/C: Ratio of test (T) evaluation to control (C) evaluation expressed as a percentage

| | | | Results | | | |
|---|---|---|---|---|---|---|
| Animal number | Sex | Sample | Route | Doses mg/kg | Parameter Evaluation MST | Percent T/C |
| 30 | | Control | | | 8.1 | |

-continued

| Animal number | Sex | Sample | Route | Doses mg/kg | Parameter Evaluation MST | Percent T/C |
| --- | --- | --- | --- | --- | --- | --- |
| 6 | Male | NSC 308847 | i.p. | 32.00 | 7.8 | 96 |
| 6 | Male | NSC 308847 | i.p. | 16.00 | 14.2 | 175 |
| 6 | Male | NSC 308847 | i.p. | 8.00 | 10.2 | 125 |
| 6 | Male | NSC 308847 | i.p. | 4.00 | 8.7 | 107 |
| 6 | Male | NSC 308847 | i.p. | 2.00 | 8.3 | 102 |
| 6 | Male | NSC 308847 | i.p. | 1.00 | 7.5 | 92 |

EXPERIMENT 4

Method

Host: Mouse $CD_2F_1$ ($CDF_1$)
Tumor: L-1210 Lymphoid leukemia
Inoculum Site: Subcutaneous
Tissue: Ascitic fluid
Level: $10^5$ cells
Route: intraperitoneal
Vehicle: acid diluted with saline
Total injections: 9
Treatment schedule (relative to tumor inoculation day): daily on days 1–9
Day of evaluation (relative to tumor inoculation day): 30
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation MST | Percent T/C |
| --- | --- | --- | --- | --- | --- | --- |
| 30 | | Control | | | 8.8 | |
| 6 | Male | NSC 308847 | i.p. | 24.00 | 11.0 | 125 |
| 6 | Male | NSC 308847 | i.p. | 16.00 | 15.3 | 173 |
| 6 | Male | NSC 308847 | i.p. | 10.00 | 12.0 | 136 |
| 6 | Male | NSC 308847 | i.p. | 7.00 | 10.7 | 121 |
| 6 | Male | NSC 308847 | i.p. | 5.00 | 10.4 | 118 |
| 6 | Male | NSC 308847 | i.p. | 0.00 | 8.9 | 101 |

EXPERIMENT 5

Method

Host: Mouse $CD_2F_1$ ($CDF_1$)
Tumor: L-1210 Lymphoid leukemia
Inoculum Site: Intraperitoneal
Tissue: Ascitic Fluid
Level: $10^5$ cells
Route: Intraperitoneal
Vehicle: Acid diluted with saline
Total injections: 9
Treatment schedule (relative to tumor inoculation day): daily on days 1–9
Day of evaluation (relative to tumor inoculation day): 30
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg.kg | Parameter Evaluation MST | Percent T/C |
| --- | --- | --- | --- | --- | --- | --- |
| 30 | | Control | | | 9.7 | |
| 6 | Female | NSC 308847 | i.p. | 24.00 | 13.3 | 137 |
| 6 | Female | NSC 308847 | i.p. | 16.00 | 17.0 | 175 |
| 6 | Female | NSC 308847 | i.p. | 10.00 | 11.4 | 117 |
| 6 | Female | NSC 308847 | i.p. | 7.00 | 11.1 | 114 |
| 6 | Female | NSC 308847 | i.p. | 5.00 | 11.0 | 113 |

EXPERIMENT 6

Method

Host: Mouse $CD_2F_1$ ($CDF_1$)
Tumor: L-1210 Lymphoid leukemia
Inoculum Site: Intraperitoneal
Tissue: Ascitic Fluid
Level: $10^4$ cells
Route: Intraperitoneal
Vehicle: Saline with Tween-80
Total injections: 9
Treatment schedule (relative to tumor inoculation day): daily on days 1–9
Day of evaluation (relative to tumor inoculation day): 30
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation MST | Percent T/C |
| --- | --- | --- | --- | --- | --- | --- |
| 33 | | Control | | | 9.2 | |
| 6 | Male | NSC 308847 | i.p. | 32.00 | 8.3 | 90 |
| 6 | Male | NSC 308847 | i.p. | 16.00 | 19.0 | 200 |
| 6 | Male | NSC 308847 | i.p. | 8.00 | 12.0 | 130 |
| 6 | Male | NSC 308847 | i.p. | 4.00 | 10.7 | 116 |
| 6 | Male | NSC 308847 | i.p. | 2.00 | 9.7 | 105 |

EXPERIMENT 7

Method

Host: Mouse $CD_2F_1$ ($CDF_1$)
Tumor: L-1210 Lymphoid leukemia
Inoculum Site: Intraperitoneal
Tissue: Ascitic Fluid
Level: $10^5$ cells
Route: Intraperitoneal
Vehicle: Acid diluted with saline
Total injections: 9
Treatment schedule (relative to tumor inoculation day): daily on days 1-9
Day of evaluation (relative to tumor inoculation day): 30
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation MST | Percent T/C |
| --- | --- | --- | --- | --- | --- | --- |
| 24 | | Control | | | 10.5 | |
| 6 | Male | NSC 308847 | i.p. | 32.00 | 8.0 | |
| 6 | Male | NSC 308847 | i.p. | 16.00 | 11.8 | 112 |
| 6 | Male | NSC 308847 | i.p. | 8.00 | 12.4 | 118 |
| 6 | Male | NSC 308847 | i.p. | 4.00 | 10.4 | 99 |
| 6 | Male | NSC 308847 | i.p. | 2.00 | 10.2 | 97 |
| 6 | Male | NSC 308847 | i.p. | 1.00 | 10.4 | 99 |

EXPERIMENT 8

Method

Host: Mouse $CD_2F$ ($CDF_1$)
Tumor: L-1210 Lymphoid leukemia
Inoculum Site: Subcutaneous
Tissue: Ascitic Fluid
Level: $10^6$ cells
Route: Intraperitoneal
Vehicle: Acid diluted with saline
Total injections: 9
Treatment schedule (relative to tumor inoculation day) daily on days 1-9
Day of evaluation (relative to tumor inoculation day): 30
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation | Percent T/C |
| --- | --- | --- | --- | --- | --- | --- |
| 30 | | Control | | | 8.5 | |
| 6 | Female | NSC 308847 | i.p. | 24.00 | 31.3 | 132 |
| 6 | Female | NSC 308847 | i.p. | 16.00 | 12.3 | 144 |
| 6 | Female | NSC 308847 | i.p. | 10.00 | 10.7 | 125 |
| 6 | Female | NSC 308847 | i.p. | 7.00 | 9.8 | 110 |
| 6 | Female | NSC 308847 | i.p. | 5.00 | 9.0 | 105 |

EXPERIMENT 9

Method

Host: CD2F1 (CDF)
Tumor: L-1210 Lymphoid leukemia
Inoculum Site: Intraperitoneal
Tissue: Ascitic Fluid
Level: $10^5$ cells
Route: Intraperitoneal
Vehicle: Saline with Tween-80
Total injections: 9
Treatment schedule (relative to tumor inoculation day): daily on days 1-9
Day of evaluation (relative to tumor inoculation day): 30
Parameter: Mean survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation MST | Percent T/C |
|---|---|---|---|---|---|---|
| 30 | | Control | | | 8.6 | |
| 6 | Male | NSC 308847 | i.p. | 32.00 | 7.7 | 89 |
| 6 | Male | NSC 308847 | i.p. | 16.00 | 17.0 | 197 |
| 6 | Male | NSC 308847 | i.p. | 8.00 | 11.7 | 136 |
| 6 | Male | NSC 308847 | i.p. | 4.00 | 9.3 | 108 |
| 6 | Male | NSC 308847 | i.p. | 2.00 | 8.7 | 101 |
| 6 | Male | NSC 308847 | i.p. | 1.00 | 9.0 | 104 |

EXPERIMENT 10

Method

Host: Mouse CD2F1 (CDF1)
Tumor: P 388 Lymphocytic leukemia
Inoculum Site: Intraperitoneal
Tissue: Ascitic Fluid
Level: $10^6$ cells
Route: Intraperitoneal
Vehicle: Saline with Tween-80
Total injections: 9
Treatment schedule (relative to tumor inoculation day): daily on days 1-9
Day of evaluation (relative to tumor inoculation day): 30
Parameter: Median survival time (MST) in days
NCI minimal activity criteria: Percent T/C $\geq$ 120
Percent T/C: Ratio of test (T) evaluation to control (C) evaluation expressed as a percentage

| Animal number | Sex | Sample | Route | Doses mg/kg | Parameter Evaluation MST | Percent T/C |
|---|---|---|---|---|---|---|
| 30 | | Control | | | 9.8 | |
| 6 | Male | NSC 308847 | i.p. | 32.00 | 6.1 | |
| 6 | Male | NSC 308847 | i.p. | 16.00 | 13.0 | 132 |
| 6 | Male | NSC 308847 | i.p. | 8.00 | 17.3 | 176 |
| 6 | Male | NSC 308847 | i.p. | 4.00 | 14.0 | 142 |
| 6 | Male | NSC 308847 | i.p. | 2.00 | 13.3 | 135 |

EXPERIMENT 11

Method

Host: Mouse CD2F1 (CDF1)
Tumor: P388 Lymphocytic leukemia
Inoculum Site: Intraperitoneal
Tissue: Ascitic fluid
Level: $10^6$ cells
Route: Intraperitoneal
Vehicle: Saline with Tween-80
Total injections: 9
Treatment schedule (relative to tumor inoculation day): daily on days 1-9
Day of evaluation (relative to tumor inoculation day): 30
Parameter: Median survival time (MST) in days
NCI minimal activity criteria: Percent T/C $\geq$ 120
Percent T/C: Ratio of test (T) evaluation to control (C) evaluation expressed as a percentage

| Animal number | Sex | Sample | Route | Doses mg/kg | Parameter Evaluation MST | Percent T/C |
|---|---|---|---|---|---|---|
| 30 | | Control | | | 11.8 | |
| 6 | Female | NSC 308847 | i.p. | 65.00 | 6.4 | |
| 6 | Female | NSC 308847 | i.p. | 32.00 | 7.3 | |
| 6 | Female | NSC 308847 | i.p. | 16.00 | 21.0 | 177 |
| 6 | Female | NSC 308847 | i.p. | 8.00 | 17.0 | 144 |

EXPERIMENT 12

Method

Host: Mouse $B_6D_2F_1$ ($BDF_1$)
Tumor: Colon 38
Inoculum Site: Subcutaneous
Tissue: Fragment, Tumor
Level: Not applicable
Route: Intraperitoneal
Vehicle: Saline with Tween-80
Total injections: 2
Treatment schedule (relative to tumor inoculation day) days 2 and 9
Day of evaluation (relative to tumor inoculation day): 20
Parameter: Median tumor weight (MTW) estimated from tumor diameter
NCI minimal activity criteria: Percent T/C $\leq$ 42
Percent T/C: Ratio of test (T) evaluation to control (C) evaluation expressed as a percentage

| Animal number | Sex | Sample | Route | Doses mg/kg | Parameter Evaluation MTW | Percent T/C |
| --- | --- | --- | --- | --- | --- | --- |
| 40 | | Control | | | 950* | |
| 10 | Male | NSC 308847 | i.p. | 64.00 | 252 | 26 |
| 10 | Male | NSC 308847 | i.p. | 32.00 | 270 | 28 |
| 10 | Male | NSC 308847 | i.p. | 16.00 | 733 | 77 |
| 10 | Male | NSC 308847 | i.p. | 8.00 | 861 | 90 |
| 10 | Male | NSC 308847 | i.p. | 4.00 | 775 | 81 |
| 10 | Male | NSC 308847 | i.p. | 2.00 | 685 | 72 |

*Excessive control no-takes

EXPERIMENT 12

Method

Host: Mouse $B_6D_2F_1$ (BDF$_1$)
Tumor: Colon 38
Inoculum Site: Subcutaneous
Tissue: Fragment, tumor
Level: not applicable
Route: Intraperitoneal
Vehicle: Saline with Tween-80
Total injections: 2
Treatment schedule (relative to tumor inoculation day): days 2 and 9
Day of evaluation (relative to tumor inoculation day): 20
Parameter: Median tumor weight (MTW) estimated from tumor diameter
NCI minimal activity criteria: Percent T/C≦42
Percent T/C: Ratio of test (T) evaluation to control (C) evaluation expressed as a percentage

| Animal number | Sex | Sample | Route | Doses mg/kg | Parameter Evaluation MTW | Percent T/C |
| --- | --- | --- | --- | --- | --- | --- |
| 30 | | Control | | | 1250 | |
| 10 | Female | NSC 308847 | i.p. | 128.00 | Deaths before evaluation | |
| 10 | Female | NSC 308847 | i.p. | 64.00 | 699 | 55 |
| 10 | Female | NSC 308847 | i.p. | 32.00 | 1005 | 80 |
| 10 | Female | NSC 308847 | i.p. | 16.00 | 1256 | 100 |
| 10 | Female | NSC 308847 | i.p. | 8.00 | 1100 | 88 |

EXPERIMENT 13

Method

Host: Mouse $B_6D_2F_1$ (BDF$_1$)
Tumor: Colon 38
Inoculum Site: Subcutaneous
Tissue: Fragment, tumor
Level: Not applicable
Route: Intraperitoneal
Vehicle: Saline with Tween-80
Total injections: 2
Treatment schedule (relative to tumor inoculation day): Days 2 and 9
Day of evaluation (relative to tumor inoculation day): 20
Parameter: Median tumor weight (MTW) estimated from tumor diameter
NCI minimal activity criteria: Percent T/C≦42
Percent T/C: Ratio of test (T) evaluation to control (C) evaluation expressed as a percentage

| Animal number | Sex | Sample | Route | Doses mg/kg | Parameter Evaluation MTW | Percent T/C |
| --- | --- | --- | --- | --- | --- | --- |
| 40 | | Control | | | 2403* | |
| 10 | Male | NSC 308847 | i.p. | 128.00 | Deaths before evaluation | |
| 10 | Male | NSC 308847 | i.p. | 64.00 | 700 | 29 |
| 10 | Male | NSC 308847 | i.p. | 32.00 | 1146 | 47 |
| 10 | Male | NSC 308847 | i.p. | 16.00 | 2474 | 102 |

EXPERIMENT 14

Method

Host: Mouse $B_6D_2F_1$ (BDF$_1$)
Tumor: Colon 38
Inoculum Site: Subcutaneous
Tissue: Fragment, tumor
Level: not applicable
Route: Intraperitoneal
Vehicle: Saline with Tween-80
Total injections: 2
Treatment schedule (relative to tumor inoculation day): Days 2 and 9
Day of evaluation (relative to tumor inoculation day): 20
Parameter: Median tumor weight (MTW) estimated from tumor diameter
NCI minimal activity criteria: Percent T/C≦42
Percent T/C: Ratio of test (T) evaluation to control (C) evaluation expressed as a percentage

| Animal number | Sex | Sample | Route | Doses mg/kg | Parameter Evaluation MTW | Percent T/C |
| --- | --- | --- | --- | --- | --- | --- |
| 40 | | Control | | | 1922 | |
| 10 | Female | NSC 308847 | i.p. | 64.00 | 1132 | 58 |
| 10 | Female | NSC 308847 | i.p. | 32.00 | 1013 | 52 |
| 10 | Female | NSC 308847 | i.p. | 16.00 | 2743 | 142 |
| 10 | Female | NSC 308847 | i.p. | 8.00 | 1687 | 87 |
| 10 | Female | NSC 308847 | i.p. | 4.00 | 1872 | 97 |
| 10 | Female | NSC 308847 | i.p. | 2.00 | 2141 | 111 |

EXPERIMENT 15

Method

Host: Mouse $B_6D_2F_1$ (BDF$_1$)
Tumor: Colon 38
Inoculum Site: Subcutaneous
Tissue: Fragment, tumor
Level: not applicable
Route: Intraperitoneal
Vehicle: Saline with Tween-80
Total injections: 2

Treatment schedule (relative to tumor inoculation day): Days 2 and 9
Day of evaluation (relative to tumor inoculation day): 20
Parameter: Median tumor weight (MTW) estimated from tumor diameter
NCI minimal activity criteria: Percent T/C ≦ 42
Percent T/C: Ratio of test (T) evaluation to control (C) evaluation expressed as a percentage

| Animal number | Sex | Sample | Route | Doses mg/kg | Parameter Evaluation MTW | Percent T/C |
| --- | --- | --- | --- | --- | --- | --- |
| 40 | | Control | | | 2086* | |
| 10 | Female | NSC 308847 | i.p. | 128.00 | Deaths before evaluation | |
| 10 | Female | NSC 308847 | i.p. | 64.00 | 368 | 17 |
| 10 | Female | NSC 308847 | i.p. | 32.00 | 1440 | 69 |
| 10 | Female | NSC 308847 | i.p. | 16.00 | 2261 | 108 |

*MTW in control outside its normal limits.

EXPERIMENT 16

Method

Host: Mouse $B_6C_3F_1$
Tumor: B16 Melanocarcinoma
Inoculum Site: Intraperitoneal
Tissue: Homogenate (or brei), tumor
Level: Dilution 1:10
Route: Intraperitoneal
Vehicle: Saline with Tween-80
Total injections: Nine
Treatment schedule (relative to tumor inoculation day): daily on days 1-9
Day of evaluation (relative to tumor inoculation day): 60
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation MST | Percent T/C |
| --- | --- | --- | --- | --- | --- | --- |
| 43 | | Control | | | 17.1 | |
| 10 | Male | NSC 308847 | i.p. | 32.00 | 8.3 | |
| 10 | Male | NSC 308847 | i.p. | 16.00 | 35.0 | 87 |
| 10 | Male | NSC 308847 | i.p. | 8.00 | 20.3 | 118 |
| 10 | Male | NSC 308847 | i.p. | 4.00 | 19.3 | 112 |
| 10 | Male | NSC 308847 | i.p. | 2.00 | 17.3 | 101 |
| 10 | Male | NSC 3-8847 | i.p. | 1.00 | 17.6 | 102 |

EXPERIMENT 17

Method

Host: Mouse $B_6C_3F_1$
Tumor: B16 Melanocarcinoma
Inoculum Site: Intraperitoneal
Tissue: Homogenate (or brei), tumor
Level: Dilution 1:10
Route: Intraperitoneal
Vehicle: Saline with Tween-80
Total injections: Nine
Treatment schedule (relative to tumor inoculation day): daily on days 1-9
Day of evaluation (relative to tumor inoculation day): 60
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation MST | Percent T/C |
|---|---|---|---|---|---|---|
| 40 | | Control | | | 16.6 | |
| 10 | Female | NSC 308847 | i.p. | 32.00 | 7.0 | |
| 10 | Female | NSC 308847 | i.p. | 16.00 | 22.9 | 137 |
| 10 | Female | NSC 308847 | i.p. | 8.00 | 19.4 | 116 |
| 10 | Female | NSC 308847 | i.p. | 4.00 | 20.0 | 120 |
| 10 | Female | NSC 308847 | i.p. | 2.00 | 17.0 | 102 |
| 10 | Female | NSC 308847 | i.p. | 1.00 | 18.8 | 102 |

EXPERIMENT 18

Method

Host: Mouse $B_6C_3F_1$
Tumor: B16 Melanocarcinoma
Inoculum Site: Intraperitoneal
Tissue: Homogenate (or brei), tumor
Level: Dilution 1:10
Route: Intraperitoneal Vehicle: Saline with Tween-80
Total injections: Nine
Treatment schedule (relative to tumor inoculation day): daily on days 1-9
Day of evaluation (relative to tumor inoculation day): 60
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation | Percent T/C |
|---|---|---|---|---|---|---|
| 40 | | Control | | | 19.3 | |
| 10 | Male | NSC 308847 | i.p. | 32.00 | 6.3 | |
| 10 | Male | NSC 308847 | i.p. | 16.00 | 27.0 | 139 |
| 10 | Male | NSC 308847 | i.p. | 8.00 | 23.2 | 120 |
| 10 | Male | NSC 308847 | i.p. | 4.00 | 22.0 | 113 |

EXPERIMENT 19

Method

Host: Mouse $B_6D_2F_1$
Tumor: B16 Melanocarcinoma
Inoculum Site: Intraperitoneal
Tissue: Homogenate (or brei), tumor
Level: Dilution 1:10
Route: Intraperitoneal Vehicle: Acid diluted with saline
Total injections: Nine
Treatment schedule: (relative to tumor inoculation day): daily on days 1-9
Day of evaluation (relative to tumor inoculation day): 60
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation MST | Percent T/C |
|---|---|---|---|---|---|---|
| 40 | | Control | | | 19.9 | |
| 10 | Female | NSC 308847 | i.p. | 32.00 | 6.8 | |
| 10 | Female | NSC 308847 | i.p. | 16.00 | 31.0 | 155 |
| 10 | Female | NSC 308847 | i.p. | 8.00 | 24.3 | 122 |
| 10 | Female | NSC 308847 | i.p. | 4.00 | 22.8 | 114 |
| 10 | Female | NSC 308847 | i.p. | 2.00 | 21.9 | 110 |
| 10 | Female | NSC 308847 | i.p. | 1.00 | 19.8 | 99 |

EXPERIMENT 20

Method

Host: Mouse $B_6C_3F_1$
Tumor: B16 Melanocarcinoma
Inoculum Site: Intraperitoneal
Tissue: Homogenate (or brei), tumor
Level: Dilution 1:10
Route: Intraperitoneal Vehicle: Acid diluted with saline
Total injections: Nine
Treatment schedule (relative to tumor inoculation day): daily on days 1-9
Day of evaluation (relative to tumor inoculation day): 60
Parameter: Median survival time (MST) in days
NCI minimal activity criteria: Percent T/C ≧ 125
Percent T/C: Ratio of test (T) evaluation to control (C) evaluation expressed as a percentage

| Animal number | Sex | Sample | Route | Doses mg/kg | Parameter Evaluation MST | Percent T/C |
| --- | --- | --- | --- | --- | --- | --- |
| 43 | | Control | | | 18.8 | |
| 10 | Female | NSC 308847 | i.p. | 32.00 | 6.7 | |
| 10 | Female | NSC 308847 | i.p. | 16.00 | 20.8 | 110 |
| 10 | Female | NSC 308847 | i.p. | 8.00 | 20.9 | 111 |
| 10 | Female | NSC 308847 | i.p. | 4.00 | 20.0 | 106 |
| 10 | Female | NSC 308847 | i.p. | 2.00 | 18.3 | 97 |
| 10 | Female | NSC 308847 | i.p. | 0.00 | 18.3 | 97 |

EXPERIMENT 21

Method

Host: Mouse
Tumor: M5076 ovarian carcinoma
Inoculum Site: Intraperitoneal
Tissue: Ascitic fluid
Level: $10^6$ cells.
Route: Intraperitoneal
Vehicle: Acid diluted with saline
Total injections: 4
Treatment schedule (relative to tumor inoculation day): every 4 days for 4 times
Day of evaluation (relative to tumor inoculation day): 60
Parameter: Mean survival time (MST) in days
NCI minimal activity criteria: Percent T/C $\geq$ 125.
Percent T/C: Ratio of test (T) evaluation to control (C) evaluation expressed as a percentage.

| Animal number | Sex | Sample | Route | Doses mg/kg | Parameter evaluation | Percent T/C |
| --- | --- | --- | --- | --- | --- | --- |
| 10 | Female | NSC 208847 | i.p. | 72.00 | Toxic. | — |
| 10 | Female | NSC 308847 | i.p. | 36.00 | 37.0 | 139 |
| 10 | Female | NSC 308847 | i.p. | 18.00 | 30.8 | 115 |
| 10 | Female | NSC 308847 | i.p. | 9.00 | 28.7 | 107 |
| 10 | Female | NSC 308847 | i.p. | 4.50 | 29.0 | 109 |
| 50 | Female | Control | | | 26.6 | |

EXPERIMENT 22

Method

Host: Mouse
Tumor: M5076 ovarian carcinoma
Inoculum Site: Intraperitoneal
Tissue: Ascitic fluid
Level: $10^6$ cells.
Route: Intraperitoneal
Vehicle: Acid diluted with saline
Total injections: 4
Treatment schedule (relative to tumor inoculation day): every 4 days for 4 times
Day of evaluation (relative to tumor inoculation day): 60
Parameter: Mean survival time (MST) in days
NCI minimal activity criteria: Percent T/C $\geq$ 125.
Percent T/C: Ratio of test (T) evaluation to control (C) evaluation expressed as a percentage.

PRECLINICAL TOXICOLOGY

SUMMARY:

Intravenous injections of benzisoquinolinedione produced reversible toxicity to the hematopoietic system, kidney and liver in male and female dogs on both single and five daily dose schedules. Signs indicative of pain and/or neurotoxicity were seen in X1 and X5 dogs at the highest doses administered. There were no deaths in dogs given a single injection of 18.4 mg/kg (2XMELD10) or five daily injections of 11..4 mg/kg/day (3XMELD10). No drug-related gross or microscopic lesions were found in any dog.

In rats, benzisoquinolinedione was toxic on both schedules (X1, X5) to the hematopoietic system and to the male reproductive system. Additional toxicities noted in rats on the X5 schedule were: gastrointestinal, tail lesions and possibly hepatotoxicity. Toxicity to the hematopoietic system and gastrointestinal tract was reversible. Toxicity to the testes and tails was delayed and had not reversed by day 36 (terminal sacrifice). The only deaths observed were one-half of the females dosed at 2XMELD10 on the X5 schedule.

More extensive information about preclinical toxicology can be found in annex 2.

PHARMACEUTICAL DATA

Tentative specifications for the bulk new pharmaceutical substance are defined in annex 3a.

Dosage form development with solution stability information is showed in annex 3b.

From these data quantitative composition of the dosage form is:

| COMPONENT | AMOUNT/VIAL |
| --- | --- |
| Nafidamide | 100 mg |
| Hydrochloric Acid. | To adjust pH |
| Sterile water for injection. USP | Removed by lyophilization |

SYNONYM

Compound of the present application is the compound of—example 9 of U.S. Pat. No. 4,204,063 and its NCI code is—NSC 308847. Other synonyms are Amonafide (Non proprietary name of OMS), Nafidimide, Benzisoquinolinedione (used in—preclinical toxicology) and its abbreviation BIDA.

Antitumor activity and preclinical toxicity of compound can be summarized as follow:

Antitumor Activity

BIDA was selected for development based on its activity against l.p. Implanted L1210 leukemia. Activity is observed over a two-fold dosing range when given l.p. and is retained when given p.o. or I.V. It was also active against s.c. Implanted L1210 and l.p. implanted P388 leukemia. Activity was seen in two non-leukemic murine tumors, M5076 sarcoma and B16 melanoma. The drug was not active against I.V. implanted Lewis lung careinoma or S.C. implanted CD8F1, mammary or colon 38 carcinomas. No activity was seen against human CX-1 colon, LX-L lung, or MX-1 mammary tumor xenografts implanted beneath the renal capsule in athymic mice (2).

Precilinical Toxicity

Preclinical toxicity studies of BIDA were completed in CD2F1 Mice, Fischer 344 rats and beagle dogs (4). The animals were injected IV with a single bolus or daily for five days. Hematopoletic, renal and hepatic toxicity were seen in dogs on both schedules. Signs indicating pain and/or neurotoxicity were seen on both schedules at the highest females and were reversible on both schedules. Some of the dogs had reddish colored urine during drug administration; further testing indicated the color was produced by the drug or its metabolites. Neither the single injection of 2×MELD10 or the daily×5 injection of the 3×MELD10 caused lethality in dogs.

In rats but not in dogs, reproductive system toxicity

Chemical Name:
1H-Benz[de]isoquinoline-1,3(2H-dione, 5-amino-2-[2-(dimothylamino)ethyl]

Other Names: Benzisoquinolinedione, BIDA (NSC 308847)

Molecular Formula: MW 283

Formulation: 100 mg drug and 1 N HCl lyophilized yield the salt. The lyophilized cake dissolves in 2 ml sterile water to yield a 50 mg/ml red solution at pH 5.0–7.0.

Stability: The reconstituted solution is stable for 14 days at room temperature. When further diluted 200-fold with normal saline the drug remains stable for 14 days at both room and refrigeration temperatures. The reconstituted solution is not stable when further diluted with 5% dextrose in water so this vehicle will not be used for infusions of the drug. Storage: The intact vials should be stored under refrigeration.

On these basis NCI has started clinical trial on several malignanacy tumors. Malignancies studied are:
renal carcinoma
colon carcinoma
adenocarcinoma, unknown primary
bladder carcinoma
head and neck carcinoma
esophageal carcinoma
NSC lung
oat cell lung carcinoma
ovarian carcinoma Doses and schedules used, up the date, in clinical trial are showed in the next table:

| STUDY | SCHEDULE | ROUTE | DOSE (mg/m²) STARTING | HIGHEST | RECOMMENDED | PATIENTS |
|---|---|---|---|---|---|---|
| M. D. Anderson Hosp. Dr. Legha | Daily × 5 Every 3-4 weeks Course 1 | i.v. | 10 | 400 | — | 11 |
| Ohio State Univeristy Comperhensive. Cancer Center Dr. Leiby | Bolus Every 3 weeks Course 2 | i.v. | 18.4 | 294.4 | — | 28 |
| Univ. Texas San Antonio Dr. Van Hoff | Daily × 5 Bolus Every 4 weeks | i.v. i.v. | 7.6 (16)220 | 91.2 — | — — | — — | was seen at doses of MELD 10 and higher. The toxicity occurred in males only and consisted of decreased testicular weights and mild diffuse testicular atrophy 29 days after receiving the drug. The toxicity was delayed, in that it was not seen on day 4 or 8. See section 6.3 for special procedures for quantitating this toxicity.

Pharmaceutical development for a new drug to be used in humans beings yield the next data:

PHARMACEUTICAL DATA

Structure

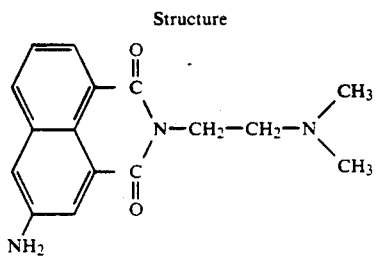

Chemical Name:
1H-Benz[de]isoquinoline-1,3(2H)-dione, 5-amino-2-[2-(dimethylamino)ethyl]

Other Names: Benzisoquinolinedione, BIDA (NSC 308847)

Molecular Formula: MW 283

Formulation: 100 mg drug and 1 N HCl lyophilized yield the salt. The lyophilized cake dissolves in 2 ml sterile water to yield a 50 mg/ml red solution at pH 5.0–7.0.

Stability: The reconstituted solution is stable for 14 days at room temperature. When further diluted 200-fold with normal saline the drugs remains stable for 14 days at both room and refrigeration temperatures. The reconstituted solution is not stable when further diluted with 5% dextrose in water so this vehicle will not be used for infusions of the drug. Storage: The intact vials should be stored under refrigeration.

On these basis NCI has started clinical trial on several malignanacy tumors. Malignancies studied are:
renal carcinoma colon carcinoma
adenocarcinoma, unknown primary
bladder carcinoma
head and neck carcinoma
esophageal carcinoma
NSC lung
oat cell lung carcinoma
ovarian carcinoma Doses and schedules used, up the data, in clinical trial are showed in the next table:

| COMPOUND | DOSE TESTED | T/C % | STATUS |
|---|---|---|---|
| 27 | 138.60 mg/kg | Toxic | |
| 27 | 69.30 | 116 | |
| 27 | 34.70 | 116 | None dose tested reached T/C > 120 |
| 27 | 17.30 | 112 | |
| 27 | 200.00 | 100 | |
| 27 | 100.00 | 101 | |
| 27 | 50.00 | 100 | |
| 11 | 48.39 mg/kg | 96 | |
| 11 | 24.20 | 160 | T/C > 120 active |
| 11 | 12.10 | 135 | T/C > 120 active |
| 11 | 6.50 | 112 | T/C > 120 active (MDA) |
| 11 | 48.39 | 86 | |
| 11 | 24.20 | 180 | T/C > 120 active |
| 11 | 12.10 | 163 | T/C > 120 active |
| 11 | 6.50 | 137 | T/C > 120 active (MDA) |
| 26 | 75.70 | 121 | T/C > 120 active |
| 26 | 37.80 | 111 | |
| 26 | 13.90 | 116 | |
| 26 | 9.50 | 110 | |
| 26 | 151.00 | <100 | |
| 26 | 75.50 | <100 | |
| 26 | 37.80 | 139 | T/C > 120 active |
| 26 | 18.90 | 132 | T/C > 120 active (MDA) |
| 26 | 151.00 | | |
| 26 | 75.50 | 119 | |
| 26 | 37.80 | 119 | |
| 26 | 18.90 | 100 | |
| 26 | 151.00 | <100 | |
| 26 | 75.50 | 96 | |
| 26 | 37.80 | 132 | T/C > 120 active |
| 26 | 18.90 | 124 | T/C > 120 active (MDA) |
| 9* | 32.00 mg/kg | <100 | |
| 9 | 16.00 | 132 | T/C > 120 active |
| 9 | 8.00 | 176 | T/C > 120 active |
| 9 | 4.00 | 142 | T/C > 120 active |
| 9 | 2.00 | 137 | T/C > 120 active (MDA) |
| 9 | 65.00 | <100 | |
| 9 | 32.00 | <100 | |
| 9 | 16.00 | 177 | T/C > 120 active |
| 9 | 8.00 | 144 | T/C > 120 active |
| 10 | 13.00 mg | 121 | T/C > 120 active |
| 10 | 6.50 | 107 | |
| 10 | 3.20 | 108 | |
| 10 | 1.60 | 100 | |
| 10 | 26.00 | 124 | T/C > 120 active |
| 10 | 13.00 | 123 | T/C > 120 active |
| 10 | 6.50 | 123 | T/C > 120 active |
| 10 | 3.20 | 127 | T/C > 120 active (MDA) |
| 10 | 100.00 | <100 | |
| 10 | 50.00 | 160 | T/C > 120 active |
| 10 | 25.00 | 114 | |
| 10 | 12.50 | 107 | |
| 10 | 6.25 | 98 | |
| 10 | 3.12 | 98 | |
| 10 | 1.56 | 101 | |
| 24 | 240.00 mg/kg | 127 | T/C > 120 active (MDA) |
| 24 | 120.00 | 117 | |
| 24 | 60.00 | 110 | |
| 24 | 240.00 | 130 | T/C > 120 active (MDA) |
| 24 | 120.00 | 100 | |
| 24 | 60.00 | 117 | |
| 24 | 30.00 | 107 | |
| 30 | 240.00 mg/kg | Toxic. | |
| 30 | 120.00 | Toxic. | |
| 30 | 60.00 | <100 | |
| 30 | 30.00 | 97 | |
| 30 | 15.00 | 195 | T/C > 120 active |
| 30 | 7.50 | 144 | T/C > 120 active |
| 30 | 30.00 | 205 | T/C > 120 active |
| 30 | 15.00 | 164 | T/C > 120 active |
| 30 | 7.50 | 145 | T/C > 120 active |
| 30 | 3.75 | 137 | T/C > 120 active (MDA) |
| 31 | 240.00 mg/kg | 206 | T/C > 120 active |
| 31 | 120.00 | Toxic. | |
| 31 | 60.00 | 184 | T/C > 120 active |
| 31 | 240.00 | <100 | |
| 31 | 120.00 | 107 | |
| 31 | 60.00 | 202 | T/C > 120 active |
| 31 | 30.00 | 186 | T/C > 120 active (MDA) |
| 4 | 240.00 mg/kg | 100 | None dose tested reached T/C ≧ 120 |
| 4 | 120.00 | 96 | |
| 4 | 60.00 | 96 | |
| 12 | 240.00 mg/kg | 114 | None dose tested reached T/C ≧ 120 |
| 12 | 120.00 | 103 | |
| 12 | 60.00 | 108 | |
| 28 | 240.00 mg/kg | 175 | T/C > 120 active |
| 28 | 120.00 | 150 | T/C > 120 active |
| 28 | 60.00 | 125 | T/C > 120 active |
| 28 | 240.00 mg/kg | <100 | |
| 28 | 120.00 | 192 | T/C > 120 active |
| 28 | 60.00 | 147 | T/C > 120 active |
| 28 | 30.00 | 123 | T/C > 120 active (MDA) |
| 29 | 240.00 mg/kg | 158 | T/C > 120 active |
| 29 | 120.00 | 135 | T/C > 120 active |
| 29 | 60.00 | 131 | T/C > 120 active |
| 29 | 240.00 mg/kg | 161 | T/C > 120 active |
| 29 | 120.00 | 147 | T/C > 120 active |
| 29 | 60.00 | 133 | T/C > 120 active |
| 29 | 30.00 | 127 | T/C > 120 active (MDA) |
| 13 | 240.00 mg/kg | 109 | None dose tested reached T/C ≧ 120 |
| 13 | 120.00 | 102 | |
| 13 | 60.00 | 102 | |
| 3 | 240.00 mg/kg | 114 | None dose tested reached T/C ≧ 120 |
| 3 | 120.00 | 103 | |
| 3 | 60.00 | 108 | |

*Data for compound 9 are presented in extension in present application.
MDA = Minor dose active.

PRECLINICAL TOXICOLOGY

SUMMARY

Intravenous injections of benzisoquinolinedione produced reversible toxicity to the hematopoietic system, kidney and liver in male and female dogs on both single and five daily dose schedules. Signs indicative of pain and/or neurotoxicity were seen in X1 and X5 dogs at the highest doses administered. There were no deaths in dogs given a single injection of 18.4 mg/kg (2XMELD10). or five daily injections of 11.4 mg/kg/day (3XMELD10). No drug-related gross or microscopic lesions were found in any dog.

In rats, benzisoquinolinedione was toxic on both schedules (X1, X5) to the hematopoietic system and to the male reproductive system. Additional toxicities noted in rats on the X5 schedule were: gastrointestinal, tail lesions and possibly hepatotoxicity. Toxicity to the hematopoietic system and gastrointestinal tract was reversible. Toxicity to the testes and tails was delayed and had not reversed by day 36 (terminal sacrifice). The only deaths observed were one-half of the females dosed at 2XMELD10 on the X5 schedule.

PRECLINICAL TOXICOLOGY

A preclinical toxicology study of benzisoquinolinedione (NSC-308847) was done at Springborn Institute for Bioresearch, Inc. using $CD_2F_1$ mice, Fischer 344 rats and beagle dogs. Animals were injected intravenously on a single dose (X1) or five daily dose (X5) regimen. Bulk drug was titrated with 0.5N HCl to form a salt solution of benzisoquinolinedione at a pH of 5.0-6.5. Sterile 0.9% saline was used for diluting the dosing solutions and was used for the vehicle control animals.

Hemolytic potential testing at a drug concentration of 50 mg/ml showed hemolysis at a 1:1 ratio of drug to canine and human whole blood. Slight hemolysis was seen at a 1:2 ratio, but none was seen at 1:4. Therefore, a concentration of 12.5 mg/ml was used in the dog studies.

Blood compatibility testing at a drug concentration of 50 mg/ml showed compatibility at a 1:1 ratio of drug to canine serum and heparinized plasma and to human serum. However, precipitation occurred at 30 minutes or less at the 1:1 ratio with heparinized human plasma. Further studies were done using heparinized plasma (two additional human donors) and with EDTA plasma (one donor). At a drug concentration of 3.13 mg/ml (1:16 drug/plasma ratio), compatibility was seen with both heparinized human plasma samples at 30 minutes. Human EDTA plasma was compatible with drug at a 1:32 drug/plasma ratio.

The following protocol studies are reported here:
X1 and X5 range-finding and lethality in mice
X1 and X5 toxicity in dogs
X1 and X5 toxicity in rats Doses administered in these studies are shown in Tables 1 and 2 for mice, Table 3 for dogs and Table 4 for rats.

MOUSE LETHALITY STUDIES

All mortality and toxic signs occurred on day 1 in both the X1 range-finding and lethality studies. Toxic signs in the X1 range-finding study were labored breathing, struggling and exophthalmus. Additional signs of toxicity noted in the X1 mouse lethality study were loss of locomotor ability, decreased activity and rough hair coats. Deaths occurred within a few minutes after dosing and were preceded by labored breathing, struggling and exophthalmus.

Mice showing loss of locomotor ability instead of struggling generally survived. All surviving animals were normal within a few hours. Only slight weight loss was seen in the X1 schedule. Body weights of treated mice were comparable to control mice at termination on day 29.

Mortality occurred between days 1 and 10 in the X5 range-finding and lethality studies. Toxic signs in the X5 range-finding study were labored breathing, exophthalmus, hyperextension of limbs, loss of locomotor ability, struggling, rough hair coat, huched posture, dehydration, increased irritability, decreased activity, swollen and necrotic tails, squinted eyes, prostration and moribundity. Additional signs of toxicity observed in the X5 lethality study were ataxia and swollen faces with closed eyes and ocular discharge. Most deaths in the X5 lethality study occurred between days 6 and 10 (three died on days 2 to 5). The deaths generally were preceded by rough hair coat, decreased activity, hunched posture and dehydration. By day 10, mice had either died or had recovered, except for tail lesions which persisted to termination on day 33. Dose-related weight loss was mild to severe initially, but body weights were comparable with control mice by termination on day 33. Males and females were similarily affected on both schedules.

DOG TOXICITY STUDIES

The following summarizes the major organ toxicities resulting from IV administration of benzisoquinolinedione to dogs.

SINGLE DOSE DOG TOXICITY STUDY 18.4 mg/kg. (2XMELD10) (lethality 0/4)

Nervous: Signs indicative of pain and/or neurotoxicity were observed immediately in the first pair of dogs (one male and one female) dosed with benzisoquinolinedione. Clinical signs included vocalizations, struggling against restraint, excessive salivation, hyperextension of all limbs and/or labored breathing. For humane reasons, an analgesic and an anesthetic, Ketaset® and Rompun® were administered to the remaining pair before dosing to alleviate the apparent pain associated with dosing. The clinical signs in these animals immediately following dosing were mild in comparison to the first pair of dogs. In addition, signs associated with Ketaset® and Rompun® administration were apparent, but did not interfere with interpretations of drug-related effects. No gross or microscopic lesions were seen.

Hematologic: Moderate leukopenia $(3.8-5.4 \times 10^3/cmm)$ found in two dogs on days 3 and 8 and in a third dog on day 4. Neutrophils were more affected than lymphocytes. The fourth dog was leukopenic on day 22, but this was not likely drug-related. No drug-related gross or microscopic lesions were found.

Renal: Mild BUN elevations were seen in all dogs on day 2 (23-32 mg/dl) and in the two long-term dogs on days 22 and 29 or 28 (23-29 mg/dl). No drug-related gross or microscopic lesions were found.

Hepatic: Mild elevations in SGOT (43-70 I.U./L) and SGPT (40-57 I.U./L) were seen in three dogs on days 2, 3 and/or 4. No drug-related gross or microscopic lesions were found.

9.2 mg/kg (MELD10) (lethality 0/4)

Renal: A slight BUN increase (22-23 mg/dl) was found in one dog on days 2 and 4. Creatinine was also slightly elevated in this dog and in a second on day 4 (1.31 mg/dl). No drug-related gross or microscopic lesions were found.

Hepatic: Mild elevations in SGPT (32-43 I.U./L) were found in three dogs on days 2 and/or 4. No drug-related gross or microscopic lesions were found.

0.92 mg/kg (1/10MELD10) (lethality 0/4)

Renal: Slight elevations in BUN (26 mg/dl) and creatinine (1.29 mg/dl) were seen in one dog on day 4. No drug-related gross or microscopic lesions were found.

Hepatic: Mild SGPT elevations (27-40 I.U./L) were seen in three dogs on day 2 and in two dogs on day 4. No drug-related gross or microscopic lesions were found.

FIVE DAILY DOSE DOG TOXICITY STUDY 11.4 mg/kg/day (3XMELD10) (lethality 0/4)

Nervous: Three of four dogs showed signs indicating nervous system toxicity such as slightly increased muscle tension, struggling against restraint and mild muscle tremors on days 2 and/or 3 immediately post-dosing. The remaining female appeared normal on all five dosing days. No drug-related gross or microscopic lesions were found.

Hematologic: Moderate leukopenia ($3.5-6.6 \times 10^3$/cmm) was seen in all four dogs with lymphocytes more affected than neutrophils. This varied among the dogs by occurring on days 2 to 8 in one, on days 4 and 8 in two and on days 8 and 15 in another. Slight decreases in hemoglobin, hematocrit and red blood cells (15-24% below pretest values) were seen in one dog on days 4 and in a second on day 8. No drug-related gross or microscopic lesions were found.

Renal: One dog had a slightly increased BUN (27 mg/dl) on day 8. No drug-related gross or microscopic lesions were found.

3.8 mg/kd/day (MELD10) (lethality 0/4) No drug-related toxicities were found.

0.38 mg/kg/day (1/10MELD10) (lethality 0/4) No drug-related toxicities were found.

VCTL No unusual observations were seen.

Special Urine Testing

Reddish colored urine was observed from 2 or 3 dogs in all three dose groups of the single dose regimen on days 1, 2 and/or 3 and from 2 or 4 dogs in the highest two dose groups of the five daily dose regimen on days 1 through 5. To determine the source of the color, the following analyses were done: HPLC and TLC (for drug); routine urinalyses, orthotolidine reagent strip and sulfosalicylic acid/ammonium sulfate precipitation tests (for occult blood). The results indicated the color was produced by the drug or its metabolites and the presence of blood was negligible.

RAT TOXICITY STUDIES

The following summarizes the major organ toxicities resulting from IV administration of benzisoquinolinedione to rats.

SINGLE DOSE RAT TOXICITY STUDY 35.0 mg/kg (MELD50) (lethality 0/20)

Hematologic: Mild decreases in hemoglobin, hematocrit and red blood cells were seen in males and females on day 4 and in only females on day 8. This was accompanied by moderate decreases in reticulocytes in both sexes on day 4, followed by moderate increases on day 8. Leukopenia (both lymphocytes and neutrophils) followed the same pattern as reticulocytes, with moderate decreases in both sexes on day 4 and moderate increases on day 8. Both sexes were comparable to controls on days 22 and 29.

No gross lesions indicative of toxicity were found. Microscopic lesions verified hematologic toxicity in short-term males and females. The day 4 lesions were: marked to severe diffuse bone marrow atrophy and mild to moderate diffuse thymic atrophy. Reversibility was shown by the lack of lesions in the long-term rats of both sexes.

Reproductive: All five male rats showed decreased testicular weights and mild diffuse testicular atrophy at the day 29 sacrifice. Since this was not seen on day 4, the reproductive toxicity was a delayed effect and reversibility of this was not evaluated in this study. No reproductive lesions were seen in females.

30.0 mg/kg (MELD10) (lethality 0/20)

Hematologic: Mild decreases in hemoglobin, hematocrit and red blood cells were seen in females on days 4 and 8, but not in males. Males and females showed moderate decreases in reticulocytes and leukocytes on day 4 with moderate increases following on day 8 in both sexes. All rats at this dose were within normal range of days 22 and 29.

Microscopic evaluation showed moderate to marked diffuse bone marrow atrophy and mild to moderate diffuse thymic atrophy on day 4 in both sexes; by day 29, no hematologic lesions were found, indicating reversal of toxicity.

Reproductive: All five long-term male rats showed decreased testicular weights on day 29 and four of five showed mild diffuse testicular atrophy at microscopic evaluation. Reproductive lesions were not seen in males on day 4, nor in females at all. Thus, reproductive toxicity was delayed and sex specific.

15.0 mg/kg (1/2MELD10) (lethality 0/20)

Hematologic: Mild decreases in leukocytes were seen in males on day 4 and mild decreases in reticulocytes were seen in females on the same day. Other hematologic indicies were within normal limits on day 4 and all rats at this dose were within normal limits on days 8, 22 and 29.

Microscopic evaluation showed mild diffuse thymic atrophy in three male rats on day 4, but not in females. No hematologic lesions were seen in either sex on day 29.

VCTL

No unusual observations were seen.

NCTL

No unusual observations were seen.

FIVE DAILY DOSE RAT TOXICITY STUDY 24.0 mg/kg/day (2XMELD10) (lethality 5/20)

Hematologic: Mild increases in hemoglobin, hematocrit and red blood cells were seen in male rats on day 8, followed by moderate to slight decreases in these parameters on days 15 and 22, respectively. By day 36, the males were comparable to controls. Females at this dose were unaffected on day 8, but none survived beyond day 9 for further evaluation. No reticulocytes were observable in either sex on day 8; however, a moderate rebound was seen on days 15 and 22 in the males. Reticulocytes remained slightly increased above control levels on day 36. Platelets and leukocytes (neutrophils and lymphocytes) followed the same pattern as reticulocytes, with marked decreases being seen on day 8, followed by moderate to marked increases above baselines on days 15 and 22. On day 36, males were comparable to controls, except for a mild thrombocytosis.

Histopathology of rats sacrificed on day 8 and females that died on day 9 confirmed the clinical pathology data with marked to severe diffuse atrophy of the bone marrow and thymus in both sexes. Moderate to marked diffuse atrophy of the spleen was found only in females. The findings were: marked to severe bone marrow atrophy (5/5 males, 10/10 females); marked to severe thymic atrophy (3/5 males, 9/10 females). Atrophy of the spleen was moderate to marked (3/10 females). By day 36, moderate bone marrow atrophy was seen in 1/5 males and moderate to severe thymic atrophy was seen in 2/5 males. No females survived at this dose for long-term evaluation.

Gastrointestinal: Diarrhea was observed on days 6 to 10 in males and days 6 to termination (day 8 or 9) in females. Microscopic evaluation of short-term rats showed mild to marked epithelial degeneration and necrosis of the duodenum, jejunum and ileum of both sexes and mild to severe colonic epithelial necrosis only in females. Additionally, mild atrophy and marked necrosis of the mesenteric lymph node was found only in females. No lesions were seen in long-term males and no females survived for the long-term evaluation.

As a probable result of the above gastrointestinal toxicity, group means body weights were depressed 29: to 30: on day 8. Clinical observations included emaciation (days 7–12) and dehydration (days 9–12). Group mean body weights for males were depressed 26: on days 15 and 22 and were depressed further to 31: on day 26. The incidences of microscopic lesions on day 8 were: mild to marked duodenal epithelial necrosis (5/5 males, 7/10 females); mild to marked duodenal epithelial degeneration (4/5 males, 5/10 females); mild to marked jejunal epithelial necrosis (4/5 males, 9/10 females); marked jejunal epithelial degeneration (4/5 males, 5/10 females); mild to marked ileal epithelial necrosis (4/5 males, 10/10 females); moderate to marked ileal epithelial degeneration (4/5 males, 5/10 females); mild to severe colonic epithelial necrosis (3/10 females); mild atrophy of mesenteric lymph node (1/10 females) and marked necrosis of mesenteric lymph node (1/10 females).

Reproductive: All five males showed decreased testicular weights on day 36 and microscopic examination confirmed testicular atrophy which was severe in 1/5, marked in 2/5 and moderate in 2/5. No reproductive lesions were seen on day 8 in males or females.

Integumentary: Clinical observations of the injection site on day 15 indicated the tail skin was friable and sloughing in males. This degeneration progressed until termination on day 36. The severity of the lesions probably accounted for the 31: body weight loss observed at termination. Microscopic examination on day 36 showed severe tail necrosis in all five males (females did not survive past day 9). Other skin lesions were found in the inguinal area of males and included: mild necrosis of the hair bulb (2/5 males on day 8) and hyperkeratosis (moderate to marked 4/5 males on day 36).

Hepatic: Microscopic examination showed multifocal liver necrosis in two females that were found dead on day 9. The lesion was of moderate severity in one and mild in the other. No changes in clinical pathology or other hepatic abnormalities were found.

12.0 mg/kg/day (MELD10) (lethality 0/20)

Hematologic: Slight decreases in hemoglobin, hematocrit and red blood cells were seen in female rats on day 8. This was accompanied by a moderate reticulocytopenia. A moderate compensatory reticulocytosis was seen on day 15 after which the females were comparable to controls in these parameters. At this dose, male rats had a mild increase in reticulocytes on day 22; all other red cell indicies were within normal limits. Females had slight to mild leukocytosis on days 15 and 22, but were within normal limits on day 36. The males had a moderate increase in WBC only on day 15. Day 8 microscopic evaluation showed mild to moderate diffuse bone marrow atrophy (4/5 females, 4/5 males). Additionally, mild thymic atrophy was seen in 1/5 males. No microscopic lesions were seen on day 36 in either sex.

Reproductive: All five male rats has a slight decrease in testicular weight on day 36, which was verified in the microscopic evaluation as moderate testicular atrophy in all males. Lesions were not seen in males on day 8 or in females at either time point.

Integumentary: Clinical observations of dry yellowish-white scaly tails were reported beginning on day 22 for females and day 31 for males. Female tails also has reddish-tan areas. Both groups had persistent findings until termination on day 36, but microscopic evaluation did not show any tail lesions, as in the higher dose group.

6.0 mg/kg (1/2MELD10) (lethality 0/20)

Hematologic: Female rats showed moderate increases in reticulocytes on days 15 and 22, followed by a moderate decrease on day 36. All other hematologic parameters were within normal limits for the females. The males were not affected. No drug-related gross or microscopic lesions were found.

VCTL

No unusual observations were seen.

NCTL

No unusual observations were seen.

TABLE 1

Defined Doses for the Single Dose Mouse Lethality Study in CD$_2$F$_1$ Mice

| Sex | Defined Dose | Estimated Dose mg/kg | Estimated Dose mg/m$^2$ | 95% Confidence Limits (mg/kg) | Slope and Heterogeneity Factor |
|---|---|---|---|---|---|
| Male | LD90 | 75.1 | 225.3 | 71.2–85.1 | Slope = 26.0 |
| | LD50 | 67.1 | 201.3 | 63.8–70.7 | Heterogeneity |
| | LD10 | 59.9 | 179.7 | 53.1–63.1 | factor = 1.0 |
| Female | LD90 | 82.1 | 246.3 | 73.0–2587.1 | Slope = 21.2 |
| | LD50 | 71.4 | 214.2 | 62.8–177.5 | Heterogeneity |
| | LD10 | 62.2 | 186.6 | 9.6–68.7 | Factor = 2.0 |
| Combined | LD90 | 78.5 | 235.5 | 74.7–86.0 | Slope = 23.1 |
| | LD50 | 69.1 | 207.3 | 66.7–72.0 | Heterogeneity |
| | LD10 | 60.8 | 182.4 | 56.6–63.4 | Factor = 1.0 |

TABLE 1

Defined Doses for the Five Daily Dose Mouse Lethality Study in CD$_2$F$_1$ Mice

| Sex | Defined Dose | Estimated Dose day | Estimated Dose day | 95% Confidence Limits (mg/kg/day) | Slope and Meterogeneity Factor |
|---|---|---|---|---|---|
| Male | LD90 | 34.2 | 102.6 | 31.8–39.8 | Slope = 17.2 |

TABLE 1-continued

Defined Doses for the Five Daily Dose Mouse Lethality Study in CD₂F₁ Mice

| Sex | Defined Dose | Estimated Dose day | day | 95% Confidence Limits (mg/kg/day) | Slope and Meterogeneity Factor |
|---|---|---|---|---|---|
| | LD50 | 28.8 | 86.4 | 26.9–30.9 | Heterogeneity |
| | LD10 | 24.3 | 72.9 | 20.8–26.2 | factor = 1.0 |
| Female | LD90 | — | — | — — | — |
| | LD50 | — | — | — — | — |
| | LD10 | — | — | — — | — |
| Combined | LD90 | 32.5 | 97.5 | 30.9–35.2 | Slope = 22.3 |
| | LD50 | 28.4 | 85.2 | 27.3–29.6 | Heterogeneity |
| | LD10 | 24.9 | 74.7 | 22.9–26.2 | Factor = 1.0 |

<sup>a</sup>Only one data point was not 0 or 100% mortality; therefore, probit values for females could not be calculated.

TABLE 3

Doses for the Dog Toxicity Studies

| | Defined Dose | mg/kg/day | mg/m²/day | Cumulative Dose mg/m² | Mortality |
|---|---|---|---|---|---|
| Single | 2XMELD10 | 18.40 | 368.0 | 368.0 | 0/4 |
| Dose | MELD10* | 9.20 | 184.0 | 184.0 | 0/4 |
| Study | 1/10MELD10 | 0.92 | 18.4 | 18.4 | 0/4 |
| Five | 3XMELD10 | 11.40 | 228.0 | 1140.0 | 0/4 |
| Daily | MELD10* | 3.80 | 76.0 | 380.0 | 0/4 |
| Dose | 1/10MELD10 | 0.38 | 7.6 | 38.0 | 0/4 |
| Study | VCTL | 0.00 | 0.0 | 0.0 | 0/4 |

*Mouse Equivalent LD10 converted from mg/m² body surface area.

TABLE 4

Doses for the Rat Toxicity Studies

| | Defined Dose | mg/kg/day | mg/m²/day | Cumulative Dose mg/m² | Mortality |
|---|---|---|---|---|---|
| Single | MELD50 | 35.00 | 210.0 | 210.0 | 0/20 |
| Dose | MELD10* | 20.00 | 180.0 | 180.0 | 0/20 |
| Study | 1/2MELD10 | 15.00 | 90.0 | 90.0 | 0/20 |
| | VCTL | 0.00 | 0.0 | 0.0 | 0/20 |
| | NCTL | 0.00 | 0.0 | 0.0 | 0/20 |
| Five | 2XMELD10 | 24.00 | 144.0 | 720.0 | 5/20** |
| Daily | MELD10* | 12.00 | 72.0 | 360.0 | 0/20 |
| Dose | 1/2MELD10 | 6.00 | 36.0 | 180.0 | 0/20 |
| Study | VCTL | 0.00 | 0.0 | 0.0 | 0/20 |
| | VCTL | 0.00 | 0.0 | 0.0 | 0/20 |

**Two females were found dead and three females were sacrificed.

We claim:

1. A method of treating a patient with leukemia, comprising administering to said patient a chemotherapeutically effective amount of N-(2-dimethylaminoethyl)-3-amino-1,8-naphthalimide.

2. The method of claim 1, wherein said N-(2-dimethylaminoethyl)-3-amino-1,8-naphthalimide is in a pharmaceutically acceptable carrier.

3. The method of claim 1, wherein said effective amount is 1–64 mg/kg of body weight.

4. A method of treating a patient with p388 leukemia or L-1210 leukemia, comprising administering to said patient a chemotherapeutically effective amount for treatment of p388 leukemia or L-1210 leukemia of N-(2-dimethylaminoethyl)-3-amino-1,8-naphthalimide.

5. The method of claim 4, wherein said N-(2-dimethylaminoethyl)-3-amino-1,8-naphthalimide is in a pharmaceutically acceptable carrier.

6. The method of claim 4, wherein said effective amount is 1–64 mg/kg of body weight.

* * * * *

UNITED STATES PATENT AND TRADEMARK OFFICE
CERTIFICATE OF CORRECTION

PATENT NO. : 5,183,821

DATED : February 2, 1993

INVENTOR(S) : Miguel Fernandez Brana et al.

It is certified that error appears in the above-identified patent and that said Letters Patent is hereby corrected as shown below:

On the title page, Item [73],

The assignee's name is spelled incorrectly, should be,

--Laboratorios Knoll, S.A.--

Signed and Sealed this

Ninth Day of November, 1993

Attest:

BRUCE LEHMAN

Attesting Officer     Commissioner of Patents and Trademarks